(12) United States Patent
Mann et al.

(10) Patent No.: US 6,551,558 B1
(45) Date of Patent: Apr. 22, 2003

(54) METHOD AND DEVICE FOR LIQUID TRANSFER WITH AN ANALYSIS APPARATUS

(75) Inventors: Karl-Heinz Mann, Weilheim (DE); Stephan Sattler, Starnberg (DE)

(73) Assignee: Roche Diagnostics GmbH, Mannheim (DE)

(*) Notice: Subject to any disclaimer, the term of this patent is extended or adjusted under 35 U.S.C. 154(b) by 0 days.

(21) Appl. No.: 09/559,191

(22) Filed: Apr. 27, 2000

(30) Foreign Application Priority Data

Apr. 28, 1999 (DE) .......................... 199 19 305

(51) Int. Cl.$^7$ .............................. B01L 3/02; G05B 1/00; G05D 9/00; G01N 1/10; A01K 63/04
(52) U.S. Cl. .................. 422/100; 422/105; 422/106; 422/108; 422/68.1; 422/63; 422/67; 435/180; 73/863.22; 73/864; 73/864.01; 73/864.11; 73/864.31; 73/304; 116/109; 116/227
(58) Field of Search .................. 422/100, 61–67, 422/68.1, 105, 106, 108; 436/180; 73/290 R, 304, 863.32, 864, 864.01, 864.11, 864.31; 116/109, 227

(56) References Cited

U.S. PATENT DOCUMENTS

| | | | |
|---|---|---|---|
| 3,754,444 A | 8/1973 | Ure et al. .................. 73/423 A |
| 4,338,279 A | 7/1982 | Orimo et al. .................. 422/64 |
| 4,451,433 A | 5/1984 | Yamashita et al. ............. 422/63 |
| 4,543,238 A | 9/1985 | Mimura et al. ................ 422/63 |
| 4,635,478 A | 1/1987 | Hope ........................... 73/292 |
| 4,647,432 A | 3/1987 | Wakatake ..................... 422/64 |
| 4,736,638 A | 4/1988 | Okawa et al. ............ 73/864.24 |
| 4,794,085 A | * 12/1988 | Jessop et al. .................. 436/54 |
| 4,818,492 A | 4/1989 | Shimizu ...................... 422/100 |
| 4,939,925 A | 7/1990 | Sakuma et al. .............. 73/61.4 |
| 5,004,582 A | 4/1991 | Miyata et al. ................ 422/56 |
| 5,045,286 A | 9/1991 | Kitajima et al. ............. 422/100 |
| 5,049,826 A | 9/1991 | Sasao ......................... 324/662 |
| 5,104,621 A | 4/1992 | Pfost et al. .................... 422/67 |
| 5,147,610 A | 9/1992 | Watanabe et al. ............. 422/64 |

(List continued on next page.)

FOREIGN PATENT DOCUMENTS

| | | | | |
|---|---|---|---|---|
| DE | 3248449 A1 | 7/1983 | ........... G01F/23/26 |
| DE | 3905622 A1 | 8/1989 | ........... G01F/13/00 |
| DE | 3909515 A1 | 10/1989 | ........... G01N/33/49 |
| EP | 0164679 A2 | 12/1985 | ........... G01N/27/22 |
| EP | 0280965 A2 | 9/1988 | ........... G01N/35/06 |
| EP | 0355791 A2 | 2/1990 | ........... G01N/35/06 |
| EP | 0555710 A3 | 8/1993 | ........... G01N/35/06 |
| GB | 2245707 A | 1/1992 | ........... G01N/27/30 |
| WO | WO88/10412 | 12/1988 | ........... G01F/23/26 |

OTHER PUBLICATIONS

U.S. patent application Ser. No. 09/181,647, Roesicke, filed Oct. 29, 1998.
Soviet patents abstracts, Section E1, Week 9337, Derwent Publications Ltd., London, GB; Class S02, AN 93–294497 & SU–A–1 763 897 (Thermal Power Instr Prodn Res Inst) Sep. 23, 1992 (1 pg).
Research disclosure No. 254, Jun. 1985, p. 296–299, disclosure No. 25430, Emsworth, Hampshire, GB; "Niveau–Fuhlanordnung fur Pipettiervorrichtung".

*Primary Examiner*—Jill Warden
*Assistant Examiner*—Brian R Gordon
(74) *Attorney, Agent, or Firm*—Brinks Hofer Gilson & Lione

(57) ABSTRACT

The invention concerns a liquid transfer device for an analysis apparatus with a liquid transfer cannula (5) and a capacitive liquid level detector to detect the immersion of the liquid transfer cannula (5) in an analysis liquid contained in a vessel. To reliably check if the liquid transfer cannula (5) is submerged in the analysis liquid or immersed for example in foam it is proposed additionally that resistance is measured by a measurement section (16) in the liquid transfer cannula (5).

27 Claims, 11 Drawing Sheets

U.S. PATENT DOCUMENTS

| | | | |
|---|---|---|---|
| 5,178,019 A | | 1/1993 | Reiter .................. 73/863.11 |
| 5,178,835 A | | 1/1993 | Uekusa et al. ............. 422/66 |
| 5,212,992 A | | 5/1993 | Calhoun et al. ....... 73/864.01 |
| 5,254,311 A | * | 10/1993 | Ushikubo ................ 422/81 |
| 5,304,347 A | | 4/1994 | Mann et al. .............. 422/67 |
| 5,855,851 A | * | 1/1999 | Matsubara et al. ....... 422/100 |
| 5,919,706 A | * | 7/1999 | Tajima ................... 436/54 |
| 5,927,547 A | * | 7/1999 | Papen et al. ............. 222/57 |
| 6,083,762 A | * | 7/2000 | Papen et al. ............. 436/180 |
| 6,107,810 A | * | 8/2000 | Ishizawa et al. ......... 324/662 |
| 6,148,666 A | * | 11/2000 | Roesicke .............. 73/290 R |
| 6,158,269 A | * | 12/2000 | Dorenkott et al. .......... 73/37 |
| 6,203,759 B1 | * | 3/2001 | Pelc et al. ............... 422/100 |
| 6,212,949 B1 | * | 4/2001 | Inder et al. ............ 73/304 R |
| 6,319,718 B1 | * | 11/2001 | Matsubara et al. ......... 436/47 |

\* cited by examiner

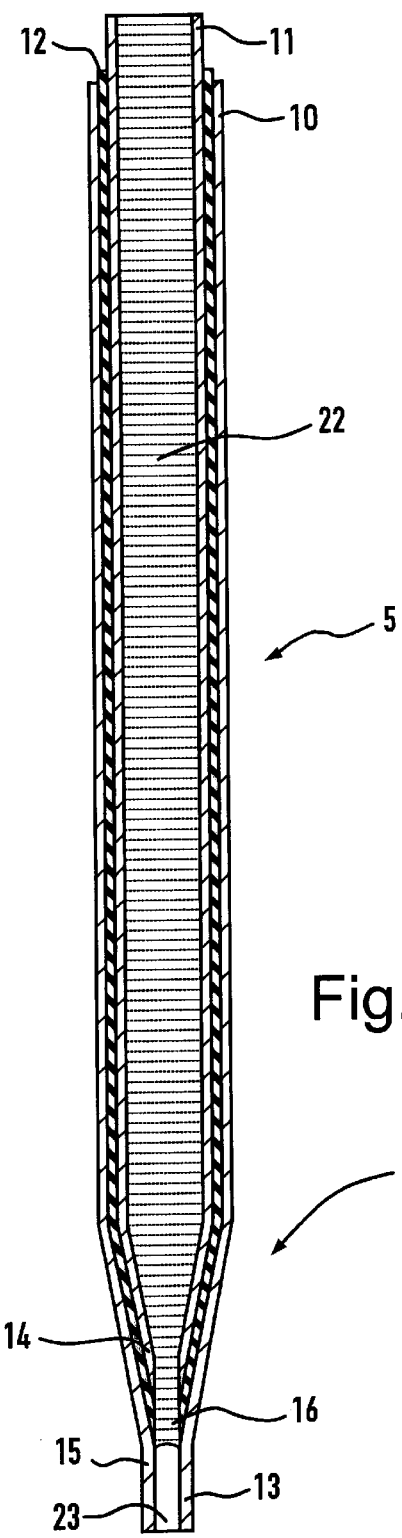
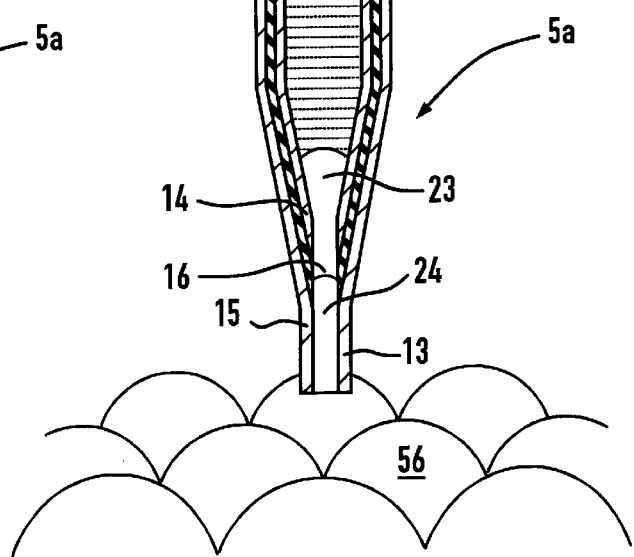

METHOD AND DEVICE FOR LIQUID TRANSFER WITH AN ANALYSIS APPARATUS

FIELD OF THE INVENTION

The invention concerns a liquid transfer device for an analysis unit having a liquid transfer cannula and a capacitive liquid level detector for detecting the dipping of the liquid transfer cannula into an analysis liquid contained in a vessel, wherein the liquid level detector has a signal electrode, a counter electrode and a detection circuit for detecting a change in capacitance between the signal electrode and the counter electrode. The invention also concerns an associated method for controlling the intake of analysis liquid into a liquid transfer cannula and a suitably designed liquid transfer cannula.

BACKGROUND OF THE INVENTION

In analysis apparatus used for analyzing body fluids, in particular of blood, liquid transfer devices are required in order to transfer analysis liquids, in particular liquid samples or reagents. Common liquid transfer devices are, for example, pipettes which are used for suction samples or reagents out of a first vessel and to expel them into a second vessel as well as dispensers with which the liquid transfer cannula is connected via a hose to a greater stock of the liquid which may be discharged through the cannulas by means of a pump device. Dispensers usually also perform the same function as a pipette.

In association with the present invention, the designation liquid transfer device generally refers to any device facilitating dipping into an analysis liquid in an analysis apparatus to effect any kind of liquid transfer operation (suctioning up and/or expulsion of liquid) using a liquid transfer cannula. The liquid transfer cannula is for example a hollow needle which normally consists of a thin tube made from metal or plastic. For reasons of simplicity this is subsequently also referred to as a cannulau. Other known forms are disposable dosing tips which are thrown away after use and replaced with new ones. They can have a tubular or tapered form, if necessary with a nozzle-type varying cross-section, can be made of metal or plastic, for example a conductive plastic, and are also described in the following as "cannula".

When the needle is immersed deeply into the analysis liquid, a relatively large amount of excess liquid remains on its outer side. As a result not only can the precision of the dosage be decreased but especially problematic is that the excess liquid contaminates another liquid into which the needle is subsequently submerged (so-called "carry-over") or an uneconomic large amount of washing agent is required.

In order to be able to better monitor the submersion depth, liquid transfer devices are provided with a sensing device for the detection of the dipping of the cannula into the analysis fluid, usually designated liquid level detectors or LLD. The liquid level detector is connected to the vertical drive used to submerge the cannula into the analysis liquid in order to stop the submersion motion when the tip of the needle has dipped a few millimeters into the analysis liquid. In addition to preventing the problem of carry-over, one must simultaneously ensure that air is not suctioned up which could lead to measurement errors affecting the diagnosis. For this reason, a minimum submersion depth must be maintained, which can be approximately between 0.1 mm and 5 mm.

The vertical position of the cannula simultaneously provides indication of the level of the liquid in the respective vessel. For this reason, the liquid level detector simultaneously facilitates monitoring of the amount of liquid in the respective vessel to issue a signal for example when the supply of a reagent liquid is used up and the reagent bottle must therefore be exchanged.

A conventional principle of construction for the liquid level detector is based on the measurement of the electrical resistance between the cannula and an electrode disposed on the cannula tip. The cannula and the electrode are electrically insulated with respect to each other so that the electrical resistance between them is very high in the dry state. When the cannula and the electrode are submerged, the sample liquid provides a conductive connection so that the electrical resistance changes abruptly. This signal can be reliably detected using simple electronics. This method has the disadvantage, however, that both the cannula and an electrode must dip into the liquid, on which unavoidable amounts of excess liquid necessarily remain. The above mentioned problem with respect to carry-over and associated reduced precision is thereby exacerbated, apart from when disposable dosing tips are used.

In this respect capacitive liquid level detectors are superior. The detection signal for dipping of the cannula into the liquid is thereby given by the change in electrical capacitance between two sensor electrodes via an electronic detection circuit including an alternating voltage source. The first electrode is thereby normally the cannula itself (which is made from metal or from an electrically conducting (metallized) plastic) and is connected to the hot terminal of the alternating voltage source (signal electrode). The counter electrode, which is usually at ground, is disposed on the outer side of the liquid container of the conventional devices (beneath its bottom and partially around the side walls of the container). This electrode is normally part of the container support. When the cannula tip enters into the liquid, the capacitance between the signal electrode and the counter electrode changes due to the electrical conductivity and dielectric properties of the liquid.

These types of liquid level detectors are described in EP-A-0 164 679, U.S. Pat. No. 4,818,492 and EP-A-0 355 791. These publications contain more detailed descriptions, the complete disclosure of which are hereby incorporated by reference.

A basic problem of capacitive liquid level detectors is that the change in capacitance when entering into the fluid is very small compared to other unavoidable capacitances ("interfering capacitances" such as the connecting cable and the input of the amplifier). The ratio between the useful signal and the interfering signal is therefore poor. A particular problem thereby is that a portion of the interfering capacitance is not constant, but can change as a function of time in a relatively rapid manner. This is particularly true for capacitive interference caused by moving objects (parts of the automated analysis system, hands or other body parts of the person using the apparatus). Particularly in fully automatic analysis apparatus having a plurality of moving components, such interferences are, in practice, unavoidable.

EP-A-0 355 791 addresses a particular problem of this kind (interference by a membrane closing the container) by setting a reference signal when the membrane contacts and during the subsequent downward motion of the needle, detecting the difference relative to this fixed reference signal. This method is directed to the particular application. Interfering capacitances which change between the fixing of the reference signal and the detection of the liquid surface lead to errors in detection.

The liquid level detector described in U.S. Pat. No. 4,818,492 passively compensates for the interfering capacitances of the leads with the assistance of a bridge circuit. Other capacitive interferences are not thereby eliminated, however, and could also lead to improper detection in this particular configuration.

A liquid transfer device for analysis apparatus having a liquid level detector with improved resistance to interference and more reliable operation is known from document EP 0555710 A2. This publication proposes a coaxial electrode configuration including the liquid transfer cannula and having an active shield via a compensation electrode connected to a voltage follower circuit. In addition, in an advantageous improvement thereof, an additional screening electrode functions as a counter electrode at constant potential.

Such a coaxial, in particular tri-axial configuration having active shielding and accompanying reference electrode facilitates, without specific adjustment or adaptation and independent of the constructive details of the surrounding apparatus, the filling amounts and the dielectric properties of the liquid, the detection of the liquid level on all positions in the apparatus which can be reached by the cannula. This is true substantially since the signal path leads from the needle tip, capacitively, to the surface of the liquid and from this point along a conceptual electric conductance along the surface of the liquid and subsequently via a capacitive signal path back to the accompanying reference electrode so that the lower portions of the liquid column have negligible effects. The liquid level detector therefore reacts extremely sensitively to capacitive changes in the vicinity of the tip so that environmental influences do not falsify detection to as great an extent.

It has, however, turned out that the extreme sensitivity in the vicinity of the tip of the liquid transfer needle can also be disadvantageous, since all moist films in the vicinity of the tip are detected as a surface of a compact, firm fluid even when the tip of the needle has not yet reached the actual surface of the liquid. In order to avoid this, special complicated error correction strategies can be developed and applied, such as subsequent displacement, plurality of insertions, pressure measurements or plausibility checks at predictable fill levels.

In particular formation of foam or soap-bubble-like structures can constitute liquid films which can falsify detection of the liquid surface. These structures are relatively long-lived and cannot necessarily be destroyed by penetration of the liquid transfer needle. Such foam layers or soap-bubble-like structures occur, e.g. when shaking a thoroughbred sample, during centrifuge operation of blood samples for the extraction of serum plasma, during transport of reagent rack-packs and by the suspending and stirring of so-called beads coated with streptavidin. These types of foam layers are normally 2 to 5 mm thick. Bubbles formed on the collar of the vessel are also not popped in many cases by the thin liquid transfer cannula.

A liquid transfer device with a capacitive liquid level detector, which solves the problem of recognizing foam by means of an additional temperature-dependent resistance was proposed in document EP 0913671 A1 published on May 6, 1999.

A further problem arising during liquid transfer consists in the fact that through errors arising improper analysis results can be obtained unwittingly if the liquid being transferred is not dosed or not correctly dosed. Reasons for this may not only be foam layers or soap-bubble-like structures on the liquid, but for example also mechanical faults of the cannula, blockages of the cannula or the cannula impinging on the bottom of the vessel.

Mechanical faults of the cannula are critical, especially if disposable dosing tips are used. These are produced by injection molding and are only inspected for faults at random. A complete check of all disposable dosing tips is not possible, so that basically there is a danger that disposable dosing tips with faults such as grooves or holes will be used unwittingly and culminate in incorrect dosing and misleading analysis results.

Blockages, which are also described as clots which can occur during intake of liquid by the cannula, or the impinging of the cannula on the vessel bottom are indeed in principal detectable due to the fact that in the attempt to suction up liquid a high vacuum builds up in the cannula. The extra cost for vacuum measurement apparatus to detect such faults is however relatively high. An especially costly method to control dosing is known in the case of an immunology-analyzer for blood banks, in which every dosing operation is controlled by means of a video camera and image processing.

With capacitive liquid level detectors dosing control has not been known up until now. Basically it would in fact be conceivable to make use of signals available from capacitive level measurement when the liquid is expelled to control dosing. The height and shape of the signals however are very dependent on the individual parameters, for example vessel form, vessel type, fill level and the conductive environment, and are therefore relatively uncertain. Control of the signals during the liquid discharge after multiple pipetting is very difficult and also unreliable on account of the various signal shapes. Also especially critical in the case of capacitive liquid level detection is that this can hardly differentiate between foam and liquid.

Apparatus to analyze liquids in which a detector created from two electrodes is arranged in the fluid channel forming a measurement section to detect air bubbles is known from documents U.S. Pat. No. 5,005,434 and EP 0527059 A1. The measurement section however is arranged in every case in the upper part of the liquid transfer cannula, which has certain disadvantages.

The air bubble detector only indicates correct liquid transfer if the measurement section between the electrodes is filled with liquid. This requires that the dosage volume is greater than the cannula volume so that dosage of small amounts of liquid in the region of a few $\mu l$ is not possible or only if more liquid is suctioned up than is ejected in the following dosing. The latter has the disadvantage of greater carry-over, less dosing precision and requires laborious washing of the cannula.

A further disadvantage is that even if the air bubble detector has recognized the presence of liquid, undetected air bubbles can exist between the lower end of the cannula tip and the air bubble detector, which leads to incorrect dosing. In addition conventional air bubble detectors are not suitable for use with disposable dosing tips since they must come into contact with the analysis liquid being transferred and therefore negate the freedom from carry-over effect achieved by replacing the disposable dosing tips. In addition no capacitive liquid level controls which are especially difficult due to the generally small change of signal when the immersion of the cannula tip in the liquid is detected are mentioned in the two documents detailed.

From U.S. Pat. No. 5,045,286 a liquid level detector is known in which the immersion of the cannula tip into the liquid is detected by measuring conductivity at the lower end of the tip. This method however is relatively slow and can lead to incorrect dosing when the tip is immersed in foam which forms a conductive film on the outside of the tip since the system does not recognize that no liquid is being suctioned up.

From U.S. Pat. No. 5,855,851 a capacitive liquid level detector is known which has additional conductivity measurement in the vicinity of the cannula tip. Conductivity is measured just above the lower end of the tip on its outside in order to check whether the tip has been submerged too deeply in liquid and must be washed. This known device cannot recognize whether air bubbles have been suctioned into the cannula but only whether undesirable liquid exists on the outside.

SUMMARY OF THE INVENTION

The aim of the invention is to design the known capacitive liquid level detectors, especially the triaxially arrangement known from document EP 0555710 A2 with an actively shielded compensation electrode and accompanying screening electrode acting as counter electrode in such a way that they can reliably differentiate between compact solid liquid and foam or liquid films and also in the case of small dosage volumes they can check whether air or liquid has been suctioned up.

BRIEF DESCRIPTION OF THE DRAWINGS

The aim in the case of a liquid transfer device of the type described at the beginning with a capacitive liquid level detector is achieved by the fact that the liquid transfer cannula has two control electrodes between which a measurement section is formed, the control electrodes are arranged in such a way that the measurement section primarily passes inside the liquid transfer cannula, at least one of the control electrodes is arranged at a distance above the lower end of the tip of the liquid transfer cannula and the detection circuit comprises a control device which is designed to detect a change in the resistance of the measurement section occurring when the measurement section in the liquid transfer cannula is filled with analysis liquid.

The idea on which the invention is based consists in the fact that to control whether the cannula is immersed in the analysis liquid or to check whether air or liquid has been suctioned up into the liquid transfer cannula, the electrical resistance or correspondingly the electrical conductance of a measurement section which lies in the fluid channel of the liquid transfer cannula and is filled with analysis liquid when functioning properly is detected. A measurement section in this context is therefore a conductive path through analysis liquid which is contained in the cannula. Such a current path can be designed linearly or three dimensionally as a detection zone whereby the beginning and end, i.e. the terminals are the two control electrodes.

Figure 1:
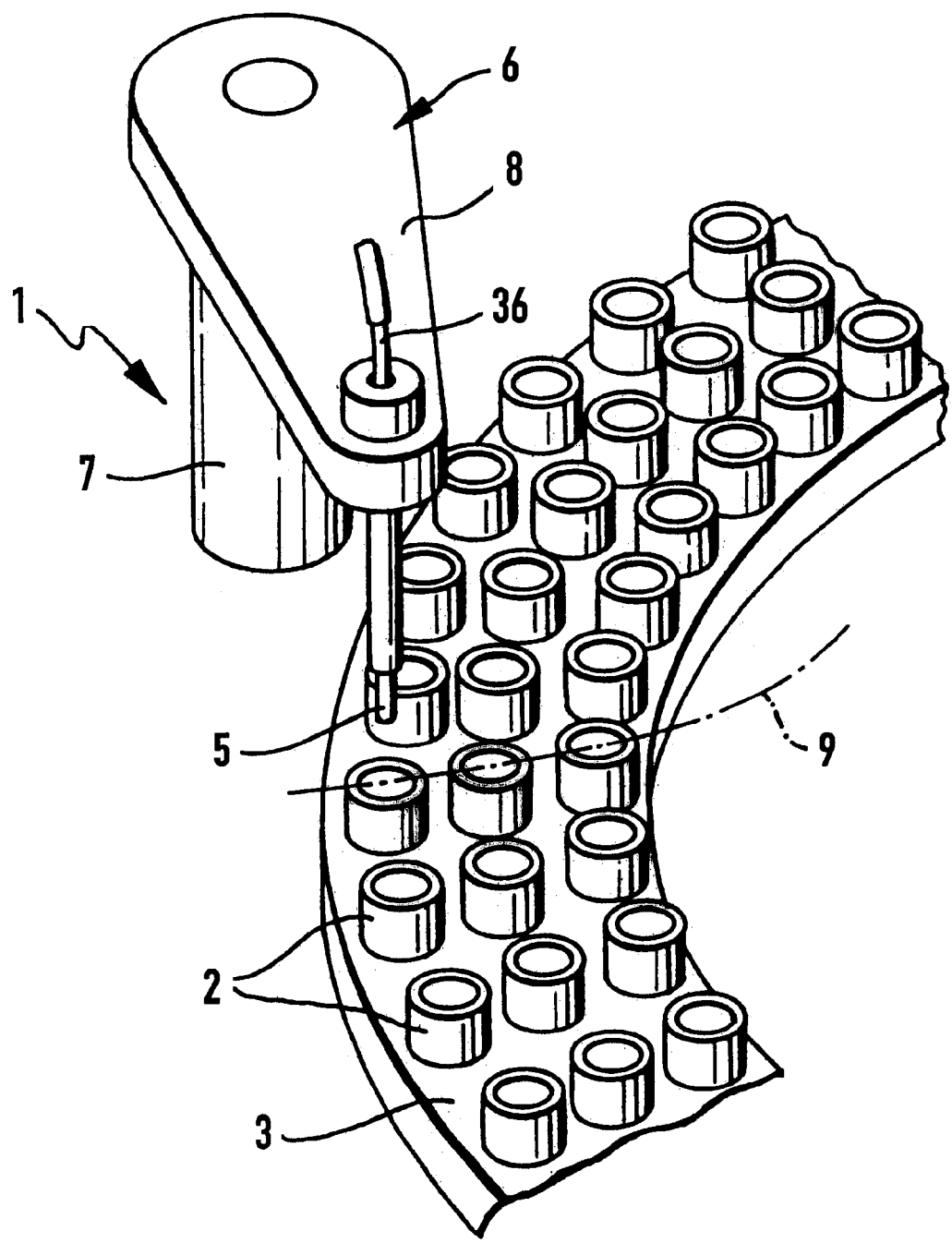

Since the electrical conductivity of analysis liquid is higher than that of air, it can be verified in this way whether the measurement section passes through air or through analysis liquid. If in line with the invention the measurement section primarily passes inside the needle and at least one of the control electrodes is above the lower end of the tip of the needle, it will be ensured that the control device can detect the immersion of the needle in foam since the foam cannot lead to greatly increased conductivity of the measurement section. The measurement section can therefore be used to check and verify submersion in a liquid detected by the capacitive liquid level detector and to recognize the intake of air in the cannula.

In principle, even a check of the conductivity of the analysis liquid by means of the measurement section alone, i.e. not in combination with a capacitive liquid level detector, could be used for detection of submersion into the analysis liquid and for recognition of air bubbles. However, such a construction is too slow for most applications to satisfy the demands on detection speed. The combination in accordance with the invention of a quickly responding capacitive liquid level detector along with a slower check by means of the measurement section in line with the invention combines the advantages of both detection possibilities.

The invention enables qualitative control of the liquid transfer with the liquid transfer cannula by monitoring the resistance of the measurement section both when taking up, as also when discharging liquid. With multiple pipetting the individual liquid stages suctioned up in the cannula and divided by separating bubbles can be identified since the separating bubbles change the resistance of the measurement section. A quantitative control of the liquid transfer is possible if the dosing rate with which analysis liquid is taken up or discharged is known and the time lapsing until the resistance of the measurement section changes is measured.

A fault in the cannula, intake of air, blockage of the fluid canal (through so-called clots) or impingement of the dosing cannula on the vessel bottom can be detected because no analysis liquid reaches or fills the measurement section and its resistance does not change. The invention therefore has the advantage that qualitative dosing control is possible whereby it is checked whether analysis liquid has been taken into the cannula or discharged by the latter. In addition quantitative dosing control of the transferred analysis liquid is possible. A further advantage lies in the fact that foam is reliably detected and the surface of the analysis liquid can be detected with certainty so that liquid transfer is always correct. No laborious vacuum measurement is necessary to register blockage of the dosing needle. Therefore the invention achieves aims for which those skilled in the art have been striving for a long time.

In accordance with a preferred additional feature, it is proposed that the liquid transfer cannula, especially the needle tip, forms one of the control electrodes. If the cannula forms one of the control electrodes, the manufacturing expense to produce and if necessary also the technical effort to measure the resistance of the measurement section is reduced. In this case the control electrode can be placed at any point in cannula by corresponding layout of the wires and suitable materials of the cannula. It is especially advantageous if the tip forms a control electrode since it will be ensured as a result that the measurement section passes almost adjacent to the tip.

Another advantageous feature can be that the measurement section is arranged at such a distance from the lower end of the tip that it passes completely through analysis liquid not when the liquid transfer cannula is submerged in the analysis liquid but only when analysis liquid is suctioned up into the liquid transfer cannula. As a result precise control of the liquid transfer by the liquid transfer cannula immersed in the analysis liquid is possible since the measurement section between the control electrodes changes resistance only when analysis liquid is taken up.

It is not necessary for the measurement section to cover the total length of the cannula. It is even desirable, to facilitate control of possibly small dosage volumes, that the measurement section covers a minimum length of the cannula and is placed not too far from its tip.

It may be advantageous if the lower end of the measurement section is arranged above the lower end of the cannula tip. As a result it is possible to slightly immerse the cannula in the analysis liquid without the lower control electrode being wetted or the measurement section already reacting to analysis liquid so that any air bubbles taken up can be reliably detected. The lower end of the measurement section is preferably between 0.5 mm and 5 mm above the lower end of the tip.

In order to be able to reliably control also small volumes of analysis liquid it is advantageous if the measurement section is adjacent to the tip so that not much analysis liquid has to be taken up into the liquid transfer cannula before a change in the resistance of the measurement section occurs. According to a further advantageous feature it is therefore proposed that the upper end of the measurement section is adjacent to the tip preferably between 0.5 mm and 30 mm above the lower end of the tip.

Additional conductivity measurement of a measurement section in combination with a capacitive liquid level detector in line with the invention is in principle advantageous with all capacitive liquid level detectors, independent of whether the capacitance of the liquid transfer cannula is measured relative to ground or whether the liquid transfer cannula is part of a coaxial electrode configuration. In general control with a measurement section is always advantageous if the capacitive liquid level detector is configured so that it is extremely sensitive to capacitance changes in its surroundings (samples, rotor, reagent vessels, static charges etc.) and in particular when it is extremely sensitive to capacitance changes around the tip of the liquid transfer cannula. On the contrary control of the measurement section will not have any substantial special advantages in recognizing foam if the mass of the detected liquid itself is incorporated into the signal path since in this case the foam or bubble formation does not substantially affect detection of the liquid surface.

The invention is therefore preferred with coaxial electrode configuration in accordance with document EP 0555710 A2 to which full reference is made in this respect i.e. in the case of coaxial electrode configurations which advantageously have active shielding via a compensation electrode connected to a voltage follower circuit and/or a screening electrode as counter electrode and extending into the region of the tip of the liquid transfer cannula.

A first preferred additional feature can therefore consist in the fact that the liquid transfer cannula is part of a coaxial electrode configuration which has, in addition to the liquid transfer cannula, at least one coaxial electrode surrounding same and insulated therefrom. An additional advantageous design feature consists in the fact that the coaxial electrode configuration has a screening electrode surrounding the signal electrode, wherein the screening electrode lies at a constant potential and acts as counter electrode.

Another advantageous feature can be that the detection circuit has an AC voltage source and a voltage follower circuit and the input and output of the voltage follower circuit are connected to two neighboring electrodes of the coaxial electrode configuration constituting signal electrode and compensation electrode so that there is no voltage difference between the signal electrode and compensation electrode and the capacitance between the signal electrode and the compensation electrode is compensated. In accordance with a further advantageous feature it can be possible that a first electrode of the coaxial electrode configuration is the signal electrode of the liquid level detector and is connected with the input of the voltage follower circuit and a second electrode of the coaxial electrode configuration adjacent to the signal electrode is connected with the output of the voltage follower circuit.

Advantageously it is also possible that the liquid transfer cannula as signal electrode is connected with the input of the voltage follower circuit and the adjacent coaxial electrode as compensation electrode with the output of the voltage follower circuit.

Figure 2:
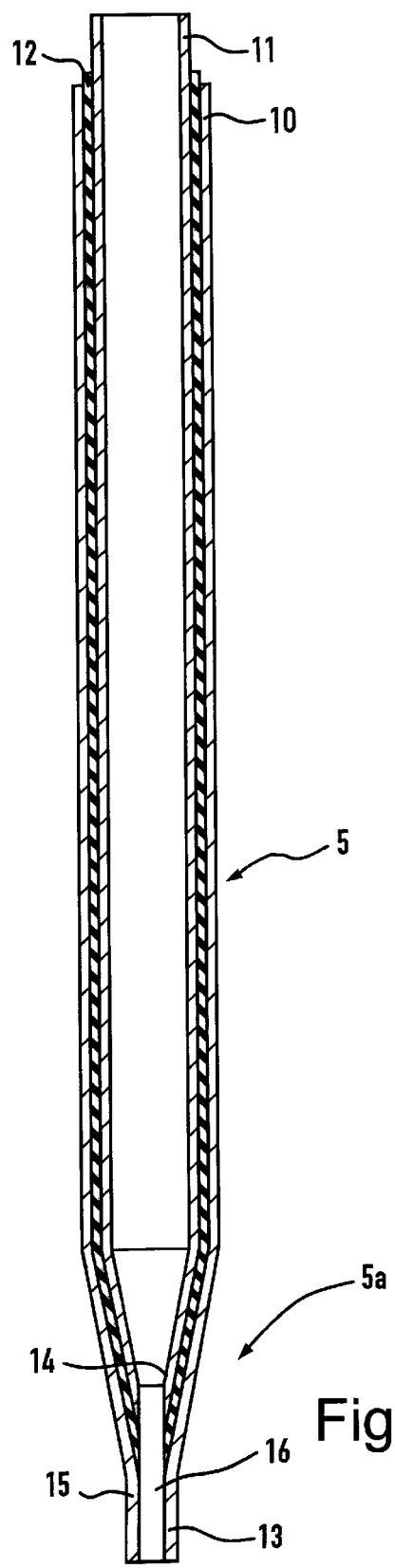
Figure 3:
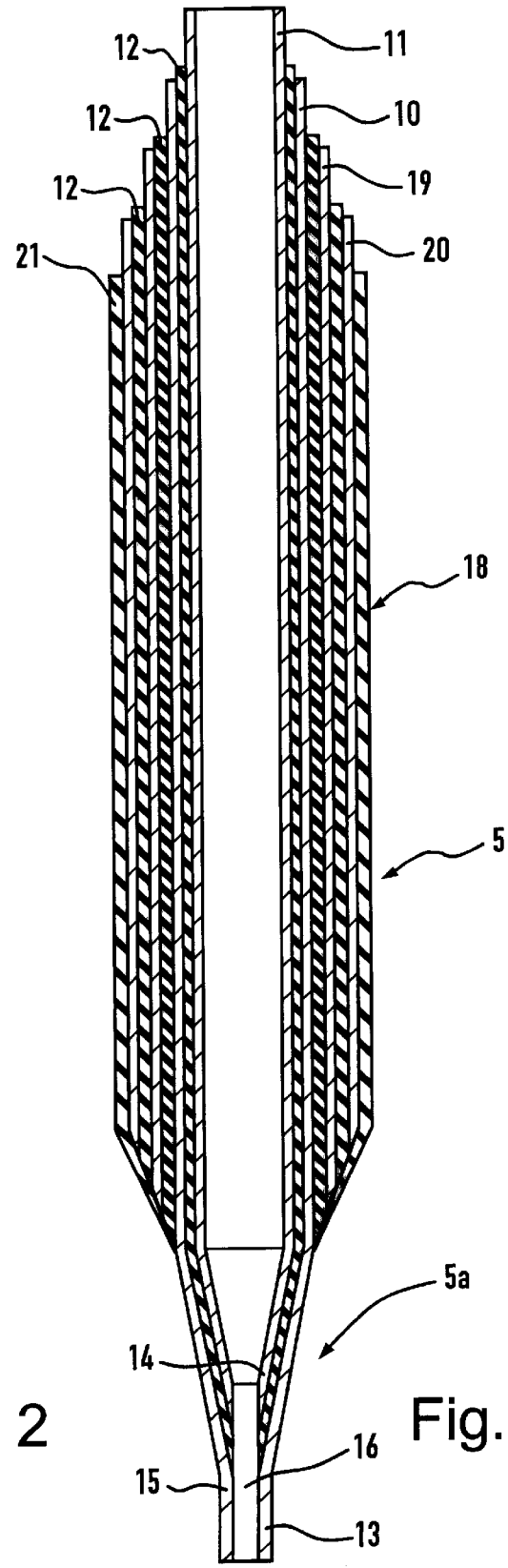
Figure 4:
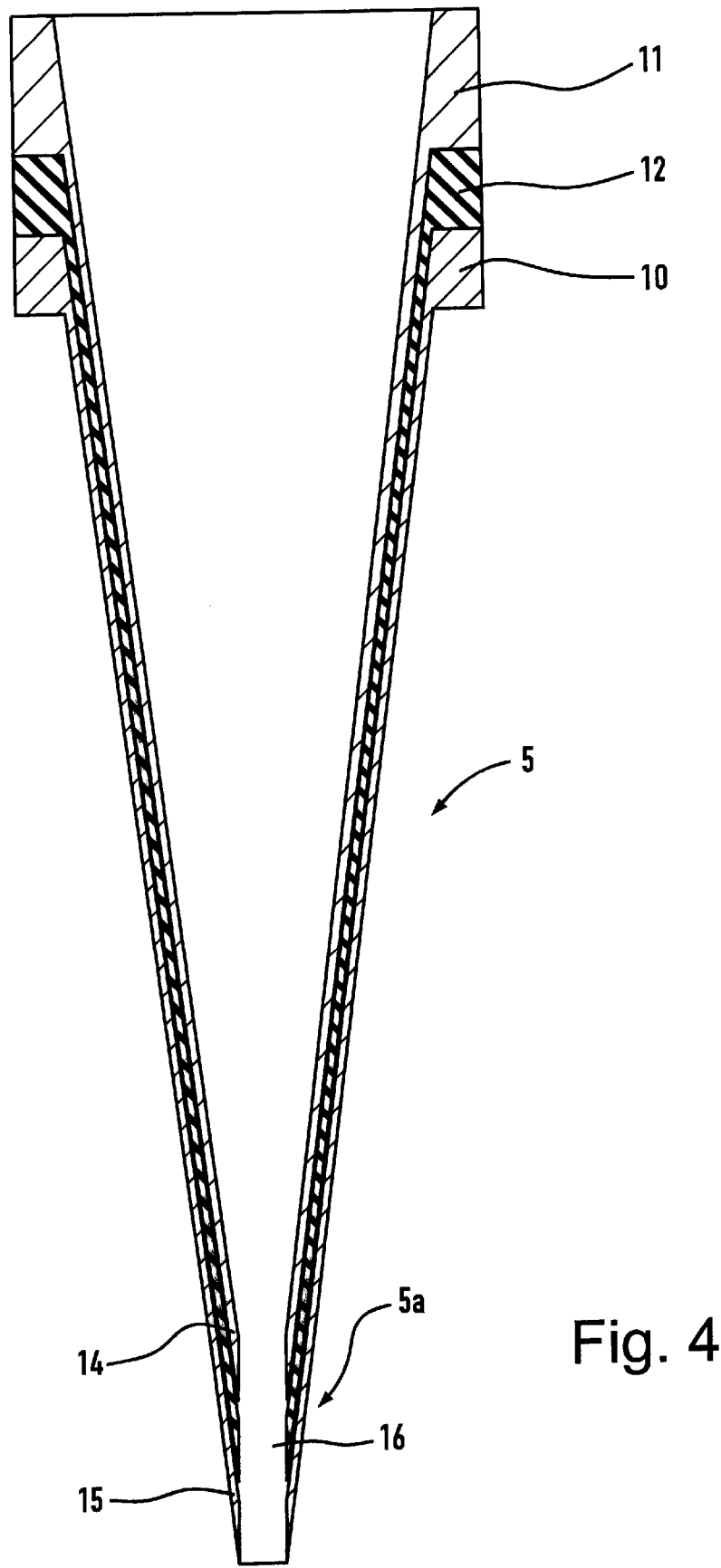
Figure 7:
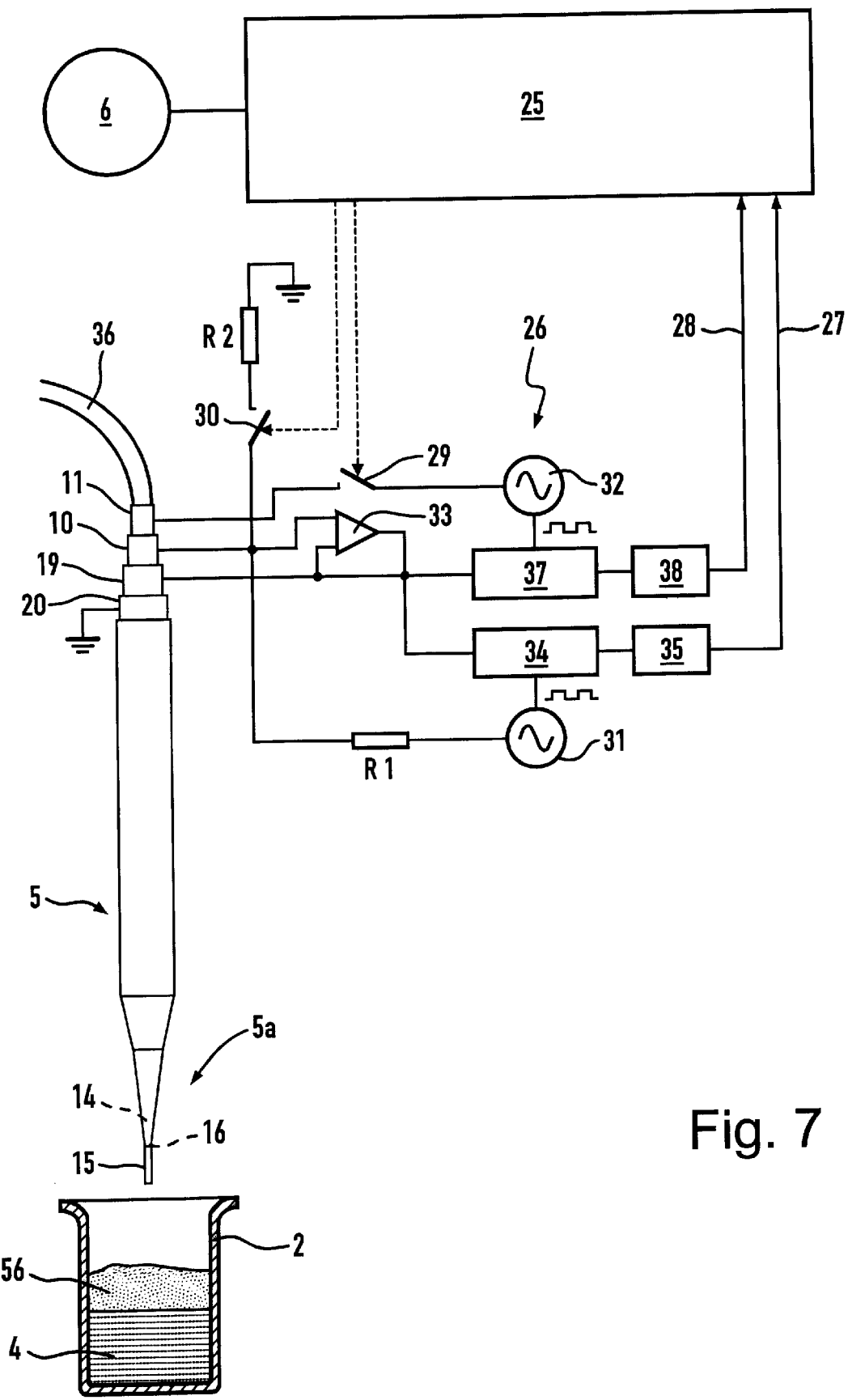
Figure 8:
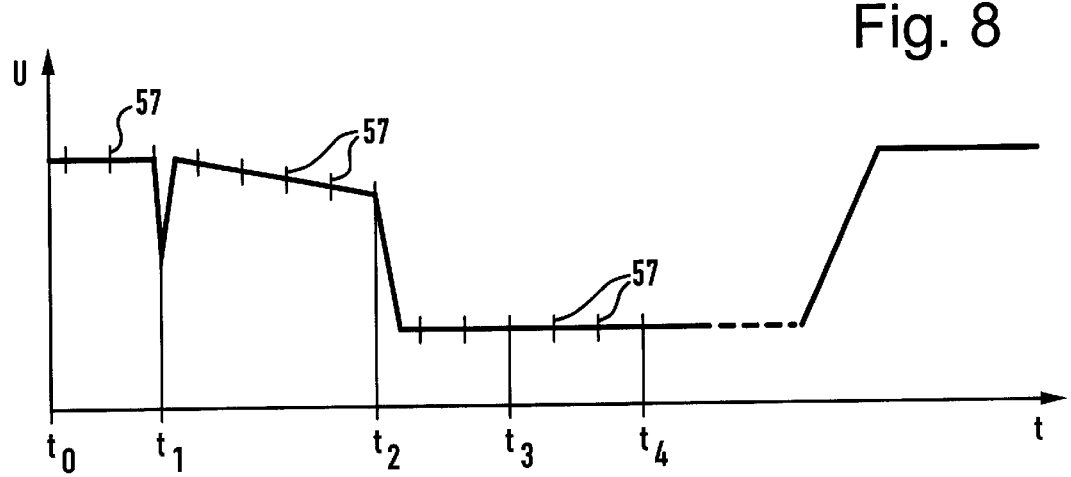
Figure 9:
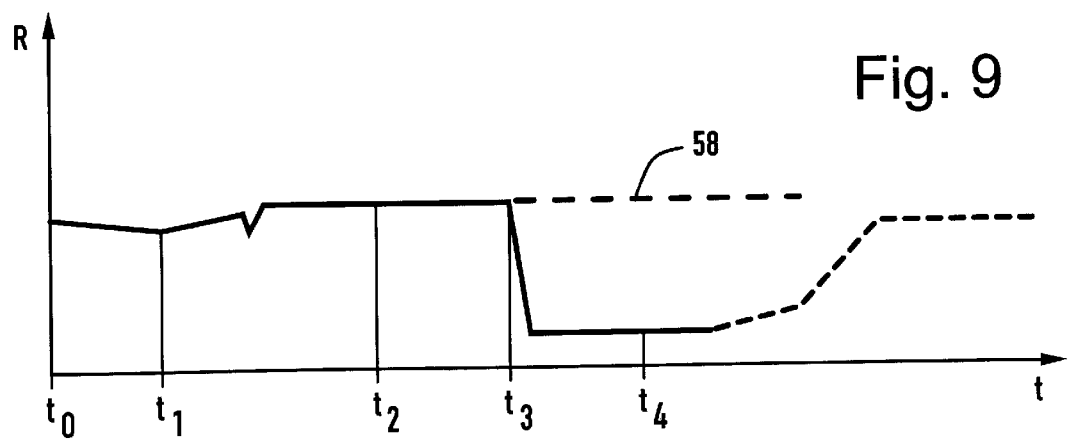
Figure 10:
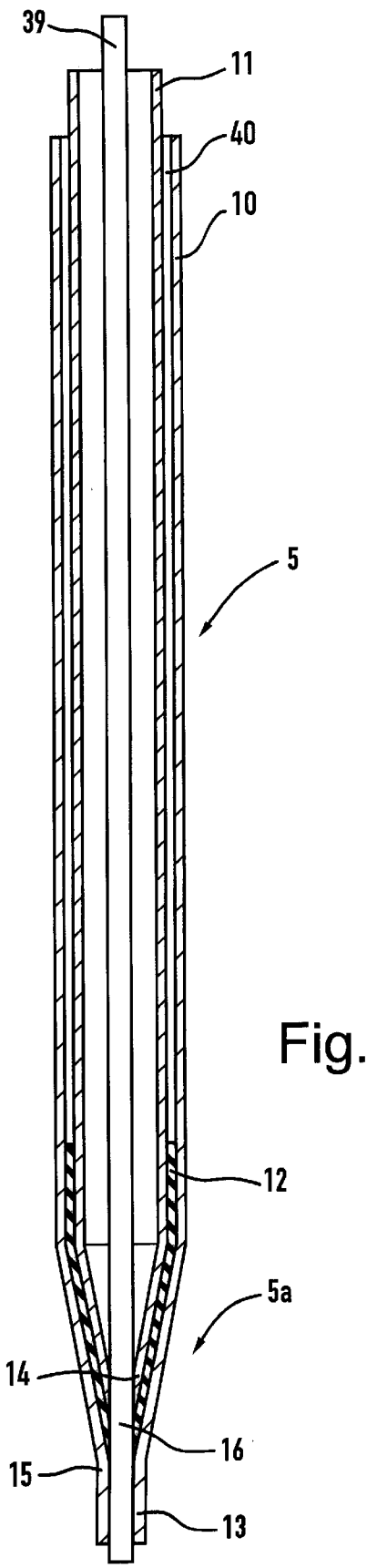
Figure 11:
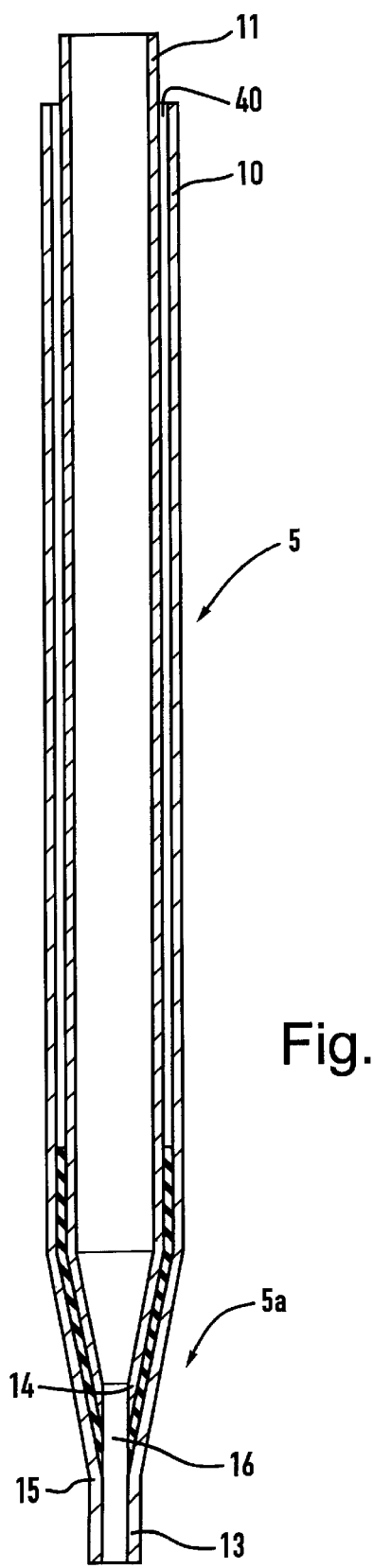
Figure 12:
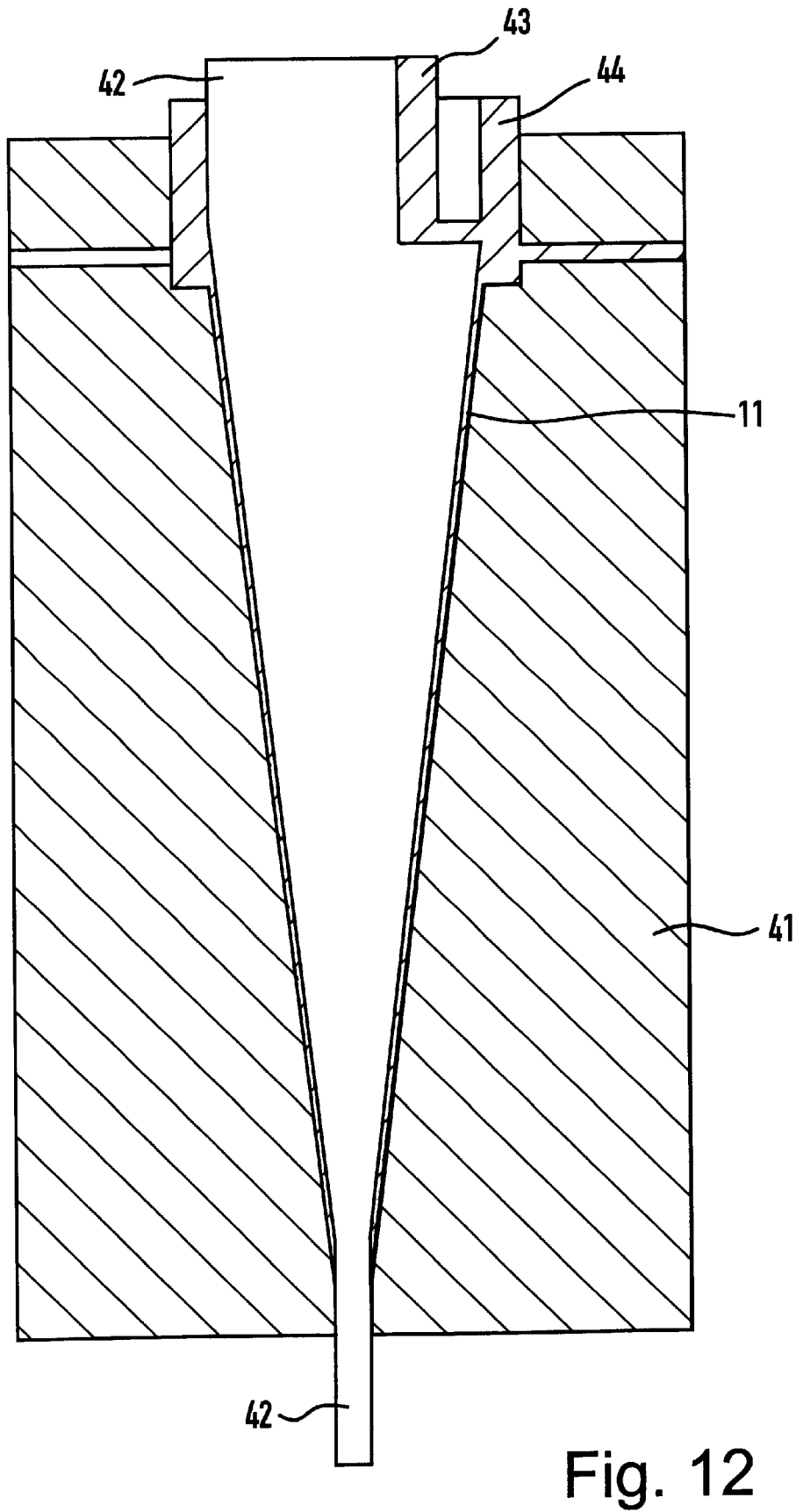
Figure 13:
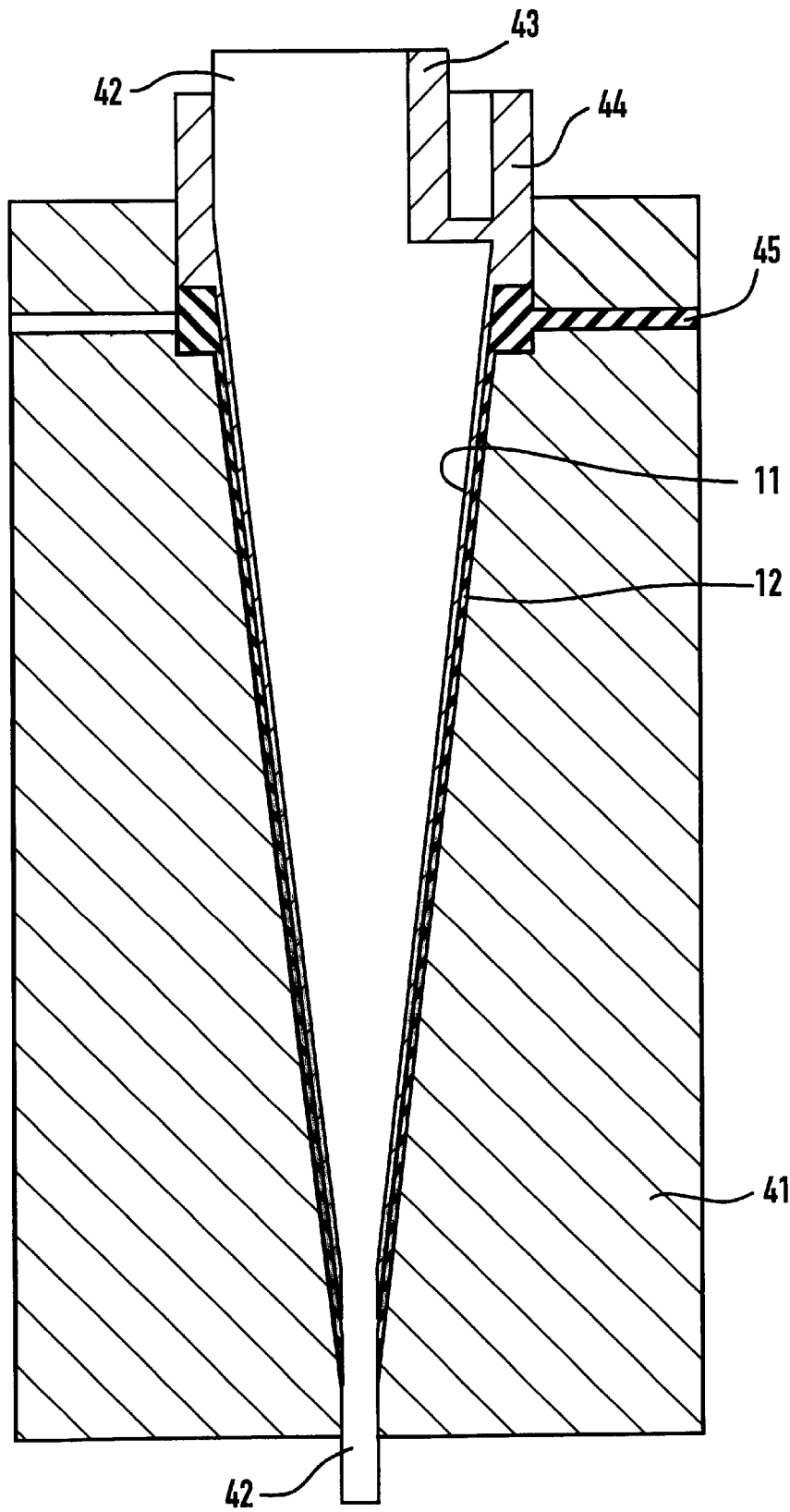
Figure 14:
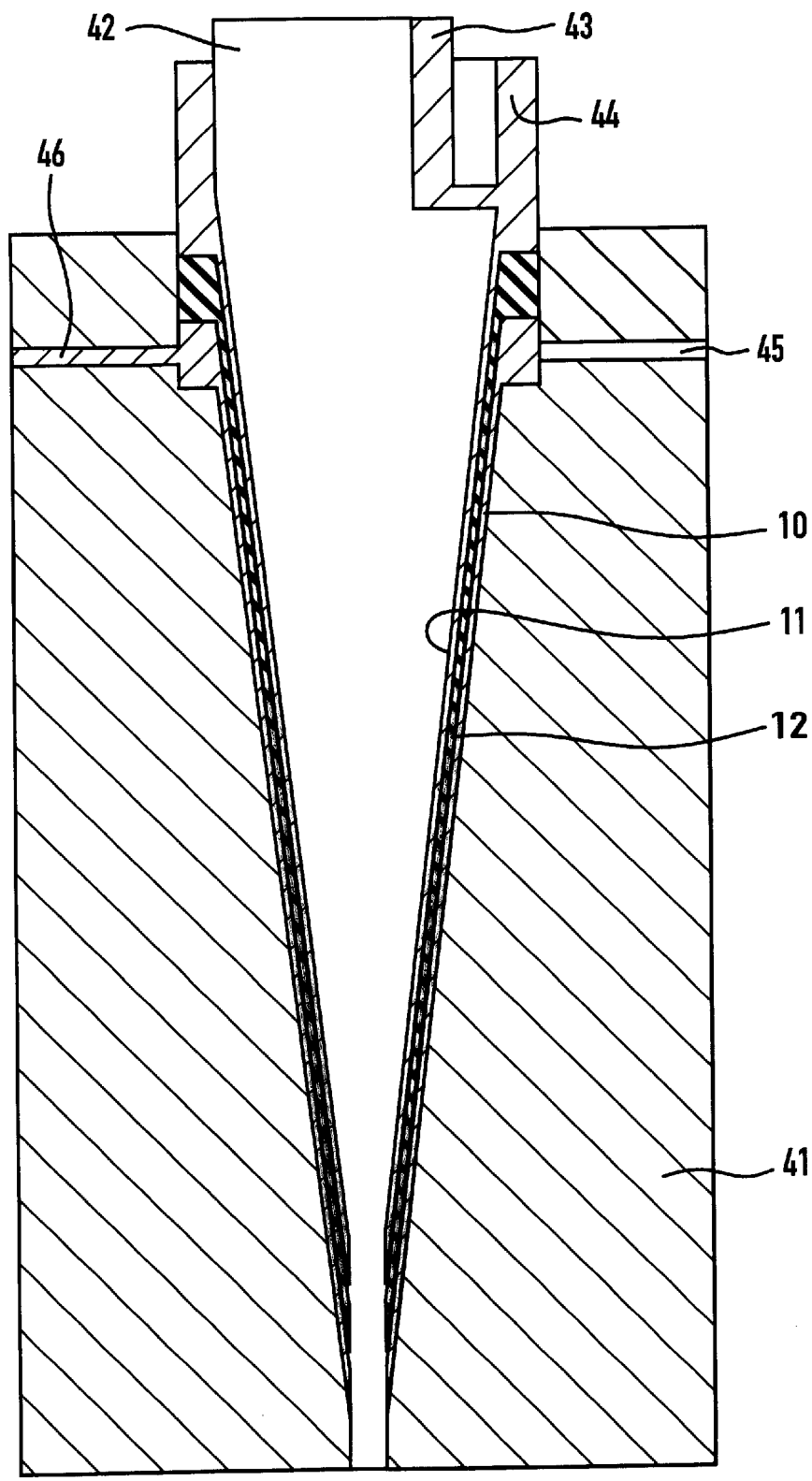
Figure 15:
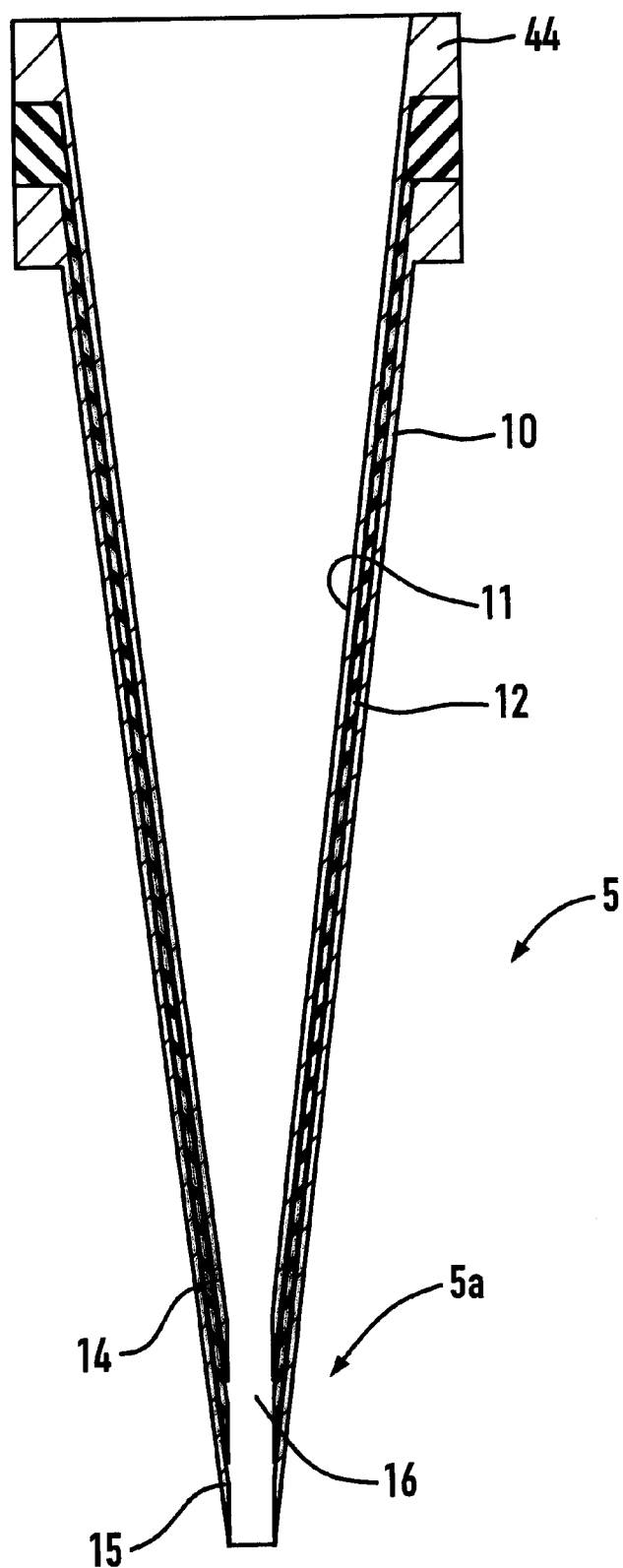

The invention is further described below with reference to embodiments schematically shown in the figures:

FIG. 1 shows a liquid transfer device in perspective view,

FIG. 2 shows a cut representation of a first liquid transfer cannula in line with the invention, FIG. 3 shows a cut representation of a second liquid transfer cannula in line with the invention, FIG. 4 shows a third liquid transfer cannula in the form of a disposable dosing tip in line with the invention, FIG. 5 shows the liquid transfer cannula of FIG. 2 with system liquid, FIG. 6 shows the liquid transfer cannula of FIG. 5 when suctioning up foam, FIG. 7 shows a cut representation of a coaxial electrode configuration combined with a schematic diagram of the detection circuit FIG. 8 shows a time diagram of a capacitive liquid level detector, FIG. 9 shows a time diagram of a measurement section, FIG. 10 shows a detail in the production of a liquid transfer cannula in accordance with FIG. 2, FIG. 11 shows a further detail in the production of a liquid transfer cannula in accordance with FIG. 2, FIG. 12 shows a first step in the production of a liquid transfer cannula in accordance with FIG. 4, FIG. 13 shows a second step in the production of a liquid transfer cannula in accordance with FIG. 4, FIG. 14 shows a third step in the production of a liquid transfer cannula in accordance with FIG. 4 and FIG. 15 shows the liquid transfer cannula regarding FIGS. 12 to 14.

DETAILED DESCRIPTION OF THE PRESENTLY PREFERRED EMBODIMENTS

The liquid transfer device 1 shown in FIG. 1 removes an analysis liquid from one of the vessels 2 and transfers it into another vessel. The vessels 2 are located on a rotor 3 or another kind of movable vessel support. In practice automatic analysis apparatus normally comprises a plurality of vessel supports. The vessel volumes assume values of approximately 400 µl to 40 ml and the transferred fluid amount approximately 10–100 µl with a resolution of approximately 0.25 µl. For incubation at 37° C. the liquids are dispensed in micro-cuvettes on an incubation rotor and the fill level must also be determined thereby.

A liquid transfer cannula 5, having an inner diameter of approximately 0.4 mm, is mounted on a cannula transport device 6 having a vertical column 7 which can be moved up and down by means of a vertical drive not shown, as well as a pivot arm 8. In this manner, the cannula 5 can be positioned along the pivot circle 9 at various locations is and lowered into one of the vessels 2. Such liquid transfer devices are known in the art in various embodiments. Reference is made to EP-A-0 408 804 with regard to a suitable drive mechanism.

FIG. 2 shows a cut representation through a first liquid transfer cannula 5 which is formed as a needle in line with the invention. It comprises two concentric tubes 10, 11 which are made from metal or a conductive plastic and are electrically insulated from each other by means of an insulating material 12. The tubes 10, 11 extend pointedly in the region of the tip 5a of the cannula 5 whereby the outer tube 10 has a straight add-on piece 13 at the lower end.

The outer tube 10 forms the signal electrode of a capacitive liquid level detector to detect immersion of the cannula 5 into an analysis liquid. The cannula 5 is lowered in the direction of an analysis liquid with a motorized drive. As soon as the tip 5a touches liquid or foam the capacitive liquid level detector recognizes contact with a conductive medium. To achieve a minimum immersion depth the drive carries on for a further distance so that the tip 5a is sufficiently immersed. Then the dosing pump suctions up a particular volume from the analysis liquid by means of the auxiliary fluid contained inside the cannula 5 which can be air or a system liquid. When using a system liquid or in the case of multiple pipetting it is advantageous if small separating air bubbles exist between the individual liquid stages sucked up.

The lower end of the inner tube 11 ends above the lower end of the tip 5a of the cannula 5. The lower sections of the inner tube 11 and the outer tube 10 in each case form a control electrode 14, 15 between which a measurement section 16 is formed. The control electrodes 14, 15 are conductively connected—which can be detected—by the analysis liquid suctioned up.

When the cannula 5 is immersed in the analysis liquid and analysis liquid is suctioned up by means of the dosing pump, it can be checked via the measurement section 16 whether analysis liquid has been taken up. If during the lowering motion the cannula 5 has not reached the liquid surface but has stopped in foam, mainly air is suctioned in. The electrical conductivity caused as a result between the control electrodes 14, 15 along the measurement section 16 is less than when analysis liquid is taken up so that it is possible to determine whether analysis liquid or foam has been suctioned up. Also other error sources possibly arising when dosing analysis liquid can be recognized in this way by means of the measurement section 16.

The liquid transfer cannula 5 is preferably part of a coaxial electrode configuration. Reference is made to documents EP 0555710 A2 and EP 0913671 A1 in regard to advantageous details of a coaxial electrode configuration, electronic circuit, the advantages and possible alternatives and variants.

An embodiment shown in FIG. 3 of a coaxial electrode configuration 18 of a liquid transfer cannula 5 comprises a coaxial electrode 19 acting as compensation electrode of an active shield and a screening or counter electrode 20 serving as shielding. Between the individual electrodes there is insulating material 12, which if necessary can be a dielectricum. The outer side of the cannula 5 can be coated with a protective coating 21, which for example can consist of an insulating material.

The outer tube 10 serving as signal electrode is completely surrounded in the radial direction about its entire perimeter by the compensation electrode 19 and the screening or counter electrode 20 and is fixed in space relative to these electrodes. The coaxial electrode is thereby a fixed part of a coaxial electrode configuration 18 extending in the axial direction along a substantial length of the liquid transfer cannula 5 with the exception of the tip 5a so that no relative motion occurs between the outer tube 10 and the surrounding electrodes. The compensation electrode 19 and the screening electrode 20 are moved upwards and downwards along with the liquid transfer cannula 5 by means of a needle transport device or, conversely, the vessel is lifted and lowered along with the analysis liquid in the direction towards the liquid transfer cannula 5.

Due to the active shielding via the compensation electrode 19 during this relative movement between liquid transfer cannula 5 and the analysis liquid, the outer tube 10 serving as signal electrode is generally shielded so that not the entire cannula length is connected capacitively to all conductive parts in its environment, but essentially the unshielded tip 5a, protruding a short distance at the lower end. Therefore the capacitance or a change in capacitance is only detected where appropriate for the capacitive liquid level detection.

In FIG. 4 a liquid transfer cannula 5 according to the invention is illustrated which is designed in the form of a disposable dosing tip. Its structure corresponds to that of the cannula 5 shown in FIG. 2, with the difference that it tapers away at the tip. It comprises three concentric layers of plastic, of which the outer 10 and inner 11 are conductive and the center consists of an insulating material 12. Also here the lower sections of the layers 10, 11 in each case form a control electrode 14, 15, between which a measurement section 16 is created, which is at a distance from the lower end of the tip 5a and extends over an area running in the longitudinal direction of the cannula 5.

In FIG. 5 the cannula 5 of FIG. 2 is illustrated when dosing with system liquid 22 and an air bubble 23. Also in this case the measurement section 16 can be used to detect the system liquid 22 and the air bubble 23 as well as to control the intake of analysis liquid. This is illustrated in FIG. 6, where a foam bubble 24 sucked from the foam 56 only results in a low conductivity of the measurement section 16, so that a detection circuit checking the conductivity between the control electrodes 14, 15 can detect that foam has been suctioned up instead of analysis liquid.

The FIG. 7 shows a schematic diagram of a detection circuit with a liquid transfer cannula 5, which corresponds to that of FIG. 3. The transport device 6 with the relevant control circuit 25 which evaluates two signals of a detection circuit 26 is illustrated schematically. The first signal 27 is that of the capacitive liquid level detection and the second signal 28 is the signal of the dosing control by means of the measurement section 16 arranged adjacent to the tip 5a of the cannula 5. The cannula 5 is connected via the hose 36 to a dosing pump not shown.

When the cannula 5 is lowered both switches 29 and 30 are opened so that the capacitive liquid level detection is not disturbed by the low impedance load resistor R2 for the conductivity measurement. The excitation voltage for the capacitive liquid level detector with a frequency of about 100 kHz is applied by the first generator 31 via a high impedance resistor R1 of approx 100 kΩ to the outer tube 10 of the cannula 5. The electrical connection to the inner tube 11 is capacitive via influence or induction, i.e. the inner tube 11 is connected electrically to the outer tube 10. When the cannula 5 is immersed the capacitance at the tip 5a changes abruptly so that the voltage on the resistor R1 changes in amplitude and phase. This change is converted into DC voltage by means of the preamplifier 33, phase rectifier 34 and low-pass filter 35 and is fed as first signal 27 which forms the signal of the capacitive liquid level detection to the control circuit 25.

After the capacitive liquid level detector has detected that the cannula 5 has touched liquid which can also be the case whenever foam or a fault is concerned, the cannula 5 is further lowered by a few millimeters to ensure minimum immersion depth by the control circuit 25 and the transport device 6. Afterwards the control by the measurement section 16 is prepared and the switches 29 and 30 are closed.

The inner tube 11 is connected with the second generator 32 by the switch 29. The second generator 32 for the detection of the conductivity of the measurement section produces a considerably lower frequency than the first generator 31; its frequency is approx 1 kHz. A resistor R2 is applied to the measurement section 16 by the switch 30. The resistor R2 is approx. 1 kΩ. As a result of the lower frequency and the small resistor R2 stray capacitive influences can be ignored i.e. conductivity measurement is facilitated.

After the switches 29 and 30 are closed the dosing pump not shown is activated by the control circuit 25 to suck up a small volume which is such that the measurement section 16 passes completely through analysis liquid taken in, provided no fault exists. If conductive analysis liquid is sucked into the measurement section 16 in the tip 5a, it forms a conductive connection between the control electrodes 14, 15. Current flows via the measurement section 16 in the analysis liquid taken in and the resistor R2 from the second generator 32 to ground.

The voltage drop at the resistor R2 proportional to the conductivity of the measurement section 16 is converted by means of the preamplifier 33, the phase rectifier 37 and the low-pass filter 38 to DC voltage which is fed as second signal 28 to the control circuit 25 in order to implement the dosing control. If the measurement section 16 has sufficiently high conductivity this means that analysis liquid has been sucked in. If the resistance of the measurement section 16 on the other hand is too high after suction an error condition exists for example air or foam has been sucked in, the cannula 5 is blocked or the hose 36 has a leak. In order to verify the error condition the cannula 5 can then be lowered step by step or continuously whereby the suction and control of conductivity of the measurement section 16 are regularly repeated or continuously carried out.

FIG. 8 shows a time diagram of the signal 27 at the output of the low-pass filter 35 when the liquid transfer cannula 5 is lowered towards the analysis liquid 4. The tip 5a is located at time t=0 at a distance from the surface of the analysis liquid 4. The lowering motion is incrementally effected, whereby the transport velocity of the cannula is approximately 1000 steps per second with a step size of 0.2 mm. It is thereby queried in regular time intervals of 1 msec whether or not the voltage has changed with a certain speed. The sampling times 57 are indicated by vertical dashes.

An interference occurs at time $t_1$ leading to a rapid transient reduction in the signal. Such an interference can for example be caused by electrostatic interference or by a popping bubble. The lowering motion of the cannula 5 is, however, not stopped by the transient rapid sinking of the signal. Rather subsequent to this event it is inquired a number of times, for example three times, whether or not a particular value remains below the last measured reference value prior to the interference. If this is not the case, for example since the bubble has broken in the meantime so that the tip 5a is therefore once more located in air, the lowering motion is continued, since it has been recognized that the tip 5a has not yet dived into the analysis liquid 4.

At time $t_2$ the signal once more decreases rapidly and remains at this low level during the plurality of subsequent samplings 57. This indicates that the tip 5a has either dived into the analysis liquid 4 or that it is located in a bubble or in foam above the analysis liquid 4 which have not reformed by the immersion. The decision which must be taken within the shortest time possible in order to prevent excessive diving of the liquid transfer cannula into the analysis fluid 4 cannot be made using the signal from the capacitive liquid level detector alone. Even for example if the sinking motion is stopped following three or four additional inquiry intervals and the possible decision conditions are fulfilled (i.e. a steep sinking of the signal is recognized by means of differentiation of the signal and triggering to a particular threshold value, comparison to a reference value prior to the trigger signal, and integration over a plurality of samplings to suppress interferences), it is nevertheless not possible to decide whether or not the tip 5a has actually dived into a dense fluid.

To solve this problem a small volume is sucked in and the signal 28 which is a measure for the resistance of the measurement section 16 and its parallel time progress is shown in FIG. 9 is used. With the interference at time $t_1$ the measurement section 16 does not react since still no analysis liquid 4 has been sucked in.

At time $t_3$ analysis liquid has been sucked in. From FIG. 9 it is clear that the resistance R of the measurement section 16 decays. This is only the case if the measurement section 16 actually passes through analysis liquid 4 sucked in. In the case of interference for example a non-burst bubble, the signal would take the alternative course 58 shown in dotted lines. Therefore it can be distinguished by the measurement of the resistance of the measurement section 16 at time $t_4$ whether the liquid transfer cannula 5, the downward motion of which has stopped for example at time $t_2$ or $t_3$ has dived into the analysis liquid 4 or not so that liquid transfer can begin or a new lowering motion can be started or the lowering motion can be continued. For a precise liquid transfer the dosing cannula could be extracted out of the liquid, the liquid already sucked up could be discharged a and then the dosing cannula again moved to the previously found position in order to complete the dosing.

A variation thereof, which is particularly interesting for time critical applications in which a very quick measurement is required so that there is no time for subsequent checking using a measurement section 16 prior to liquid transfer, provides for already initiating liquid transfer following stopping of the diving motion, i.e. at time period $t_3$ at which the capacitive checks have been completed. The measurement section 16 measurement is carried out during liquid transfer. If resistance measurement shows that the liquid transfer cannula 5 has not yet been submerged into the analysis liquid at time $t_3$ this is signaled to the analysis system and the measurement result of the current sample is retroactively discarded or a signal immediately alerts the operator that there are problems with dosing. In this manner, a higher throughput can be achieved.

The arrangement of the control electrodes 14, 15 should be of low capacitance to avoid interfering with the capacitive liquid level detector by means of stray capacitances. An advantageous embodiment thereby proposes disposing the control electrodes 14, 15, or at least a lead, between a screening electrode and a compensation electrode, the capacitance of which is compensated by a voltage follower circuit.

The measurement section 16 can also be formed between the signal electrode and a control electrode. The advantage here is that no separate leads to the measurement section 16 are needed since for example the liquid transfer cannula, the screening electrode or the coaxial electrode can be utilized as lead. This avoids additional capacitive interference to the signal being detected.

The control electrodes 14, 15 should be smooth, without protruding surfaces and should be properly mechanically mounted and electronically connected. They could also be provided with a liquid-repellent nano-coating. They could also be inserted into a depression or opening in the vicinity of the tip of the needle 5a or cast within a chemically resistive molding agent.

FIGS. 10 and 11 illustrate the production of a cannula 5 in accordance with FIG. 2. Pre-fabricated metal tubes 10, 11 are assembled concentrically to each other. A metal wire 39 which has nearly the same diameter as the dosing apertures arranged at the lower end of the metal tubes 10, 11 is fed through both metal tubes 10, 11. The gap 40 between both metal tubes 10, 11 is filled with meltable or sintable non-conductive powder or granulate. The metal wire 39 in this case serves for radial positioning of the metal tubes 10, 11 and prevents the material filled in the gap 40 being able to penetrate the dosing apertures. The metal tubes 10, 11 are heated vertically to melt and harden the material in the gap 40 whereby the insulating material 12 is formed.

The hardened insulating material 12 reaches a prescribed level in the gap 40. The gap 40 must not be completely filled; in many application cases it is sufficient if the lower ends of the tubes 10, 11 are positioned to each other by insulating material 12 without the gap being filled completely. After cooling the metal wire is drawn a out so that a cannula 5 in accordance with FIG. 11 is obtained. In order to prevent damage to the dosing aperture the metal wire 39 can be stretched before drawing as a result of which its diameter is reduced. If necessary the inside of the dosing aperture can be additionally smoothed for example by honing or a similar process.

FIGS. 12 to 15 show the production of a liquid transfer cannula 5 in the form of a disposable dosing tip in accordance with FIG. 4. In this case three layers are produced by multi-component injection molding.

FIG. 12 shows a mould 41 with a suitably sized mandrel 42 inserted in it. Firstly the inner conductive layer 11 is injected using the slip 43 in the cavity between mould 41 and mandrel 42 whereby also a wiper 44 is formed. After the layer 11 of a conductive plastic has become hard, the mandrel 42 is drawn out partly from the mould 41 and the cavity now obtained is filled by a further slip 45 to form the insulating layer 12 as shown in FIG. 13. After the insulating layer 12 has hardened the mandrel 42 is again partly drawn out of mould 41 and as shown in FIG. 14 the layer 10 from conductive plastic is injected using the slip 46. After hardening the mould is opened and the finished cannula which is shown in FIG. 15 is wiped from the mandrel 42.

LIST OF REFERENCE NUMBERS

1 Liquid transfer device
2 Vessel
3 Rotor
4 Analysis liquid
5 Liquid transfer cannula
5a Tip
6 Transport device
7 Vertical column
8 Pivot arm
9 Pivot circle
10 Outer tube
11 Inner tube
12 Insulating material
13 Add on piece
14 Control electrode
15 Control electrode
16 Measurement section
18 Coaxial electrode configuration
19 Coaxial electrode
20 Counter electrode
21 Protective coating
22 System liquid
23 Air bubble
24 Foam bubble
25 Control circuit
26 Detection circuit
27 First signal
28 Second signal
29 First switch
30 Second switch
31 First generator
32 Second generator
33 Preamplifier
34 Phase rectifier
35 low-pass filter
36 Hose
37 Phase rectifier
38 low-pass filter
39 Metal wire
40 Gap
41 Mould
42 Mandrel
43 Slip
44 Wiper
45 Slip
46 Slip
56 Foam
57 Scan times
58 Alternative course
U Voltage
t Time
R Resistance
R1 Resistor
R2 Resistor

What is claimed is:

1. A liquid transfer device for use with an analysis apparatus, the transfer device comprising:
    a liquid transfer cannula including an interior into which an analysis liquid is suctioned, said liquid transfer cannula including a tip having a lower end, a first control electrode and a second control electrode spaced from one another and defining a measurement section therebetween, said measurement section located primarily within said interior; and
    a capacitive liquid level detector comprising a detection circuit adapted to detect a change in capacitance at said tip;
    the capacitive liquid level detector adapted to detect the immersion of the liquid transfer cannula into the analysis liquid;
    said detection circuit further comprising a control device adapted to detect a change in the resistance of the measurement section when the analysis liquid enters the measurement section.

2. The liquid transfer device of claim 1, wherein at least one of said first control electrode and said second control electrode are arranged at a distance above the lower end of said tip.

3. The liquid transfer device of claim 1, wherein at least one of said first and second control electrodes is formed by said liquid transfer cannula.

4. The liquid transfer device of claim 1, wherein at least one of said first control and second control electrodes is formed by said tip.

5. The liquid transfer device of claim 1, wherein said measurement section is arranged at a distance over the lower end of said tip such that the analysis liquid does not pass through the measurement section when the liquid transfer cannula is immersed into the analysis liquid, but only when the analysis liquid is taken up into the liquid transfer cannula.

6. The liquid transfer device of claim 1, wherein a lower end of the measurement section is arranged above the lower end of said tip.

7. The liquid transfer device of claim 1, wherein a lower end of the measurement section is adjacent said tip.

8. The liquid transfer device of claim 7, wherein the lower end of the measurement section is between 0.5 mm and 5 mm above a lower end of the tip.

9. The liquid transfer device of claim 1, wherein an upper end of the measurement section is adjacent said tip.

10. The liquid transfer device of claim 9, wherein an upper end of the measurement section is between 0.5 mm and 30 mm above a lower end of the tip.

11. The liquid transfer device of claim 1, wherein said liquid transfer cannula further comprises an inner tube which forms one of said first and second control electrodes.

12. The liquid transfer device of claim 1, wherein the liquid transfer cannula is part of a dosing tip.

13. The liquid transfer device of claim 12, wherein said dosing tip comprises a disposable dosing tip.

14. The liquid transfer device of claim 1, wherein said first and second control electrodes are formed by an inner tube and an outer tube and are arranged in a coaxial configuration.

15. The liquid transfer device of claim 1, wherein said capacitive liquid level detector comprises a signal electrode, a counter electrode, and said detection circuit is adapted to detect a change in capacitance between the signal electrode and the counter electrode.

16. The liquid transfer device of claim 15, wherein at least one of said first and second control electrodes forms one of said signal electrode and said counter electrode.

17. The liquid transfer device of claim 16, wherein said first and second control electrodes are formed by an inner tube and an outer tube and are arranged in a coaxial configuration.

18. The liquid transfer device of claim 17, further comprising a screening electrode surrounding said signal electrode.

19. The liquid transfer device of claim 18, wherein said screening electrode is at constant potential and acts as a counter electrode.

20. The liquid transfer device of claim 17, wherein the detection circuit has an AC voltage source and a voltage follower circuit and an input and an output of the voltage follower circuit are connected with two adjacent electrodes of the coaxial electrode configuration such that no voltage differential occurs between them.

21. The liquid transfer device of claim 17, wherein a first electrode of the coaxial configuration is the signal electrode of the liquid level detector and is connected with an input of the voltage follower circuit and a second electrode of the coaxial configuration adjacent to said signal electrode is connected with an output of the voltage follower circuit.

22. A process for controlling a liquid transfer device of an analysis apparatus, the process comprising:

providing a liquid transfer cannula including an interior which an analysis liquid is suctioned into, said liquid transfer cannula including a tip having a lower end, and a first control electrode and a second control electrode spaced from one another and defining a measurement section therebetween, said measurement section located primarily within said interior and a capacitive liquid level detector comprising a detection circuit adapted to detect a change in capacitance at said tip;

lowering said liquid transfer cannula towards an analysis fluid;

detecting the immersion of the tip of the liquid transfer cannula in the liquid analysis fluid using the capacitive liquid level detector;

drawing analysis fluid into said interior of said liquid transfer cannula; and, measuring the resistance of the analysis fluid in the measurement section of the liquid transfer cannula.

23. The process of claim 22, wherein at least one of said first control electrode and said second control electrode are arranged at a distance above the lower end of said tip.

24. The process of claim 22, wherein the lowering of the liquid transfer cannula is carried out in incremental steps.

25. The process of claim 22, wherein the lowering is stopped only after multiple detections of immersion.

26. The process of claim 22, wherein the resistance is measured continuously.

27. The process of claim 22, wherein the resistance is measured intermittently.

* * * * *